United States Patent
Inglese et al.

(10) Patent No.: US 9,549,788 B2
(45) Date of Patent: Jan. 24, 2017

(54) OCCLUSION MAPPING USING ELASTIC FOAM MODELING

(71) Applicant: TROPHY, Rochester, NY (US)

(72) Inventors: Jean-Marc Inglese, Bussy Saint George (FR); Sabrina Capron-Richard, Noisiel (FR); Julien D. Barneoud, Bussy Saint Martin (FR); Frederic Millet, Marne la Vallee (FR); Ronan Etesse, Montreuil (FR)

(73) Assignee: TROPHY, Marne la Vallee (FR)

( * ) Notice: Subject to any disclaimer, the term of this patent is extended or adjusted under 35 U.S.C. 154(b) by 0 days.

(21) Appl. No.: 14/765,403
(22) PCT Filed: Mar. 8, 2013
(86) PCT No.: PCT/EP2013/000687
  § 371 (c)(1),
  (2) Date: Aug. 3, 2015
(87) PCT Pub. No.: WO2014/135177
  PCT Pub. Date: Sep. 12, 2014

(65) Prior Publication Data
  US 2016/0000525 A1    Jan. 7, 2016

(51) Int. Cl.
  *G06K 9/00* (2006.01)
  *A61C 7/00* (2006.01)
  (Continued)
(52) U.S. Cl.
  CPC ............. *A61C 7/002* (2013.01); *A61B 6/14* (2013.01); *A61C 9/004* (2013.01); *A61C 9/0006* (2013.01); *A61C 11/00* (2013.01)

(58) Field of Classification Search
  None
  See application file for complete search history.

(56) References Cited

U.S. PATENT DOCUMENTS

| 1,293,567 A | 2/1919 | Stanton |
| 6,334,853 B1 | 1/2002 | Kopelman et al. |
| (Continued) | | |

FOREIGN PATENT DOCUMENTS

| FR | WO 2014135177 A1 * | 9/2014 | ............ A61C 7/002 |
| WO | 2011/103876 A1 | 9/2011 | |
| WO | 2012/021816 A2 | 2/2012 | |

OTHER PUBLICATIONS

O. M. Rijal, N. A. Abdullah, Z. M. Isa, N. M. Noor and O. F.Tawfiq, "Shape model of the maxillary dental arch using fourier descriptors with an application in the rehabilitation for edentulous patient," 2013 35th Annual International Conference of the IEEE Engineering in Medicine and Biology Society (EMBC), Osaka, 2013, pp. 209-212. doi: 10.1109/EM.*

(Continued)

*Primary Examiner* — Tahmina Ansari (57) ABSTRACT

A method for generating a mapping of dental occlusion generates a three-dimensional model of the patient's teeth (1a, 1b) according to acquired image data. The maxillary and mandibular arches are positioned in opposition in the generated model of the patient's teeth and a meal model (50) generated having characteristics of a foam material. A pressure field distribution for the generated meal model is calculated for one or more pairs of opposed teeth (1a, 1b) from the generated three-dimensional model of the patient's teeth. The calculated pressure field distribution (54) can be displayed.

18 Claims, 8 Drawing Sheets (51) Int. Cl.
   *A61C 11/00*   (2006.01)
   *A61B 6/14*    (2006.01)
   *A61C 9/00*    (2006.01)

(56) References Cited

U.S. PATENT DOCUMENTS

| | | | |
|---|---|---|---|
| 7,140,877 B2 | 11/2006 | Kaza | |
| 8,992,215 B2* | 3/2015 | Chapoulaud | A61C 7/00 |
| | | | 433/24 |
| 9,208,531 B2* | 12/2015 | Boerjes | A61B 5/4547 |
| 2014/0076333 A1* | 3/2014 | Ona | A61F 5/566 |
| | | | 128/848 |
| 2016/0000525 A1* | 1/2016 | Inglese | A61C 7/002 |
| | | | 433/214 |

OTHER PUBLICATIONS

International Search Report, International application No. PCT/EP2013/000687, Mailed Jan. 7, 2014, 2 pages.

* cited by examiner

OCCLUSION MAPPING USING ELASTIC FOAM MODELING

FIELD OF THE INVENTION

The invention relates generally to the field of volumetric data collection and more particularly to apparatus and methods for occlusion mapping for the maxillary and mandibular arches within the mouth of a patient.

BACKGROUND OF THE INVENTION

Orthodontic treatment is applied for repositioning teeth and supporting structures to improve tooth function and aesthetics. In conventional orthodontic treatment, appliances such as braces are applied to the patient's teeth by an orthodontist. Over time, the continuing force exerted by the appliance can urge teeth toward more favorable positions, often providing movement to the teeth in incremental steps with successive treatments.

Aspects of tooth function that are studied as part of orthodontics and other restorative treatments include proper occlusion, so that teeth in the upper jaw work successfully with corresponding teeth in the lower jaw. Occlusion determines how opposing teeth are positioned relative to each other, come into contact, and interact with each other in normal movement.

To define a specific dental treatment such as orthodontics or a restorative treatment in conventional practice, dentists typically manipulate one or more casts obtained from a patient's dental arches. One conventional method forms an occlusogram that displays the intersection between opposite teeth, using translucent papers, for example, as described in U.S. Pat. No. 1,293,567 entitled "System of Dental Charts and Method of Making the Same" to Stanton. Using the cast, the projection of the teeth of the lower dental arch on an axial (horizontal) plane is reproduced on a first translucent paper. The projection of the teeth of the upper dental arch is reproduced on a second translucent paper. Both papers are then superimposed, providing a representation of the occlusal conditions. By dragging one of the translucent papers relative to the other, a representation of new occlusal conditions can be obtained.

With the advent of digital imaging, there have been a number of solutions proposed for representing and displaying dental occlusion using information obtained from captured image data. Information for mapping, measurement, and analysis of occlusion conditions can be digitally obtained and processed to help support the orthodontist or other dental practitioner in correcting problems and in providing the best arrangement of tooth structures for this purpose.

Methods for display of maxillary (upper) and mandibular (lower jaw) arch structures, beyond providing some idea of overall tooth registration, do not provide detailed three-dimensional (3-D) information about occlusion. Most of the occlusal surfaces are not visible in conventional cast manipulation. Cross-sectional and slice-by-slice views provide some level of detail, but only over a limited region. Even where virtual modeling techniques are used, however, information provided about occlusion is generally limited to data that identifies contact points.

Advances in the development and visualization of virtual arches provide some measure of useful information, such as data on distances between opposing occlusal surfaces, using a color-coded or gray-level encoded mapping, for example. This type of visualization can help to provide information useful for registration of the upper and lower arches. However, distance mapping yields only limited information on how teeth in the upper and lower jaws work together to chew efficiently. In practice, as the patient chews a meal, the meal is compressed between features such as cusps and ridges of opposing teeth. This type of compression generates a pressure-field that is distributed over a region. The pressure at any point over the pressure field varies, depending on factors such as distance from contact points and interaction between different pressure fields as the meal is chewed.

Because of the complex nature of information that is obtained from the interaction of opposing sets of teeth, the task of evaluating and correcting occlusion can be challenging when using conventional tools. Thus, there is a need for more accurate utilities and techniques for measuring and reporting pressure fields for occlusion.

SUMMARY OF THE INVENTION

Embodiments of the present invention address the need for improved methods for modeling occlusion for dental treatment. Embodiments of the present invention model the pressure distribution between upper and lower jaws at a given occlusal positioning and provide information that can be used for mapping the efficacy of that particular occlusion relationship. Advantageously, a virtual model can be used for manipulating jaw position to assess occlusion conditions of a patient.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

According to one aspect of the present invention, there is provided a method for generating a mapping of dental occlusion, the method comprising: generating a three-dimensional data model of the patient's teeth according to acquired image data; positioning the maxillary and mandibular arches in opposition in the generated data model of the patient's teeth; generating a meal data model having characteristics of a foam material; calculating a pressure field distribution for the generated meal data model for one or more pairs of opposed teeth from the generated three-dimensional data model of the patient's teeth; and displaying at least the calculated pressure field distribution.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

DETAILED DESCRIPTION OF THE INVENTION

The following is a detailed description of the preferred embodiments of the invention, reference being made to the drawings in which the same reference numerals identify the same elements of structure in each of the several figures.

Where they are used, the terms "first", "second", "third", and so on, do not necessarily denote any ordinal or priority relation, but may be used for more clearly distinguishing one element or time interval from another.

In the context of the present disclosure, the term "image" refers to multi-dimensional image data that is composed of discrete image elements. For 2-D (two-dimensional) images, the discrete image elements are picture elements, or pixels. For 3-D (three-dimensional) images, the discrete image elements are volume image elements, or voxels.

Figure 1:
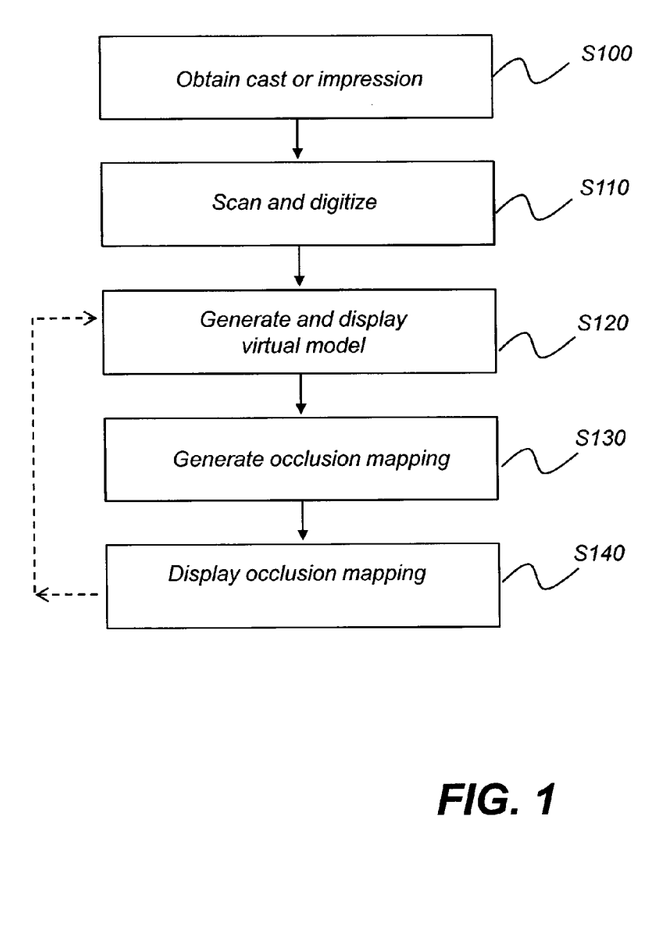
FIG. 1 is a flow diagram that shows a sequence of steps useful for providing occlusion information for a patient.

The described embodiments relate to providing information in a form that is useful for examining the arrangement of structures of the dental arches for displaying each dental arch in a useful way for the practitioner. The logic flow diagram of FIG. 1 shows a sequence of steps that are used for providing information on occlusion for a patient. In an optional preparation step S100, the dental staff obtains one or more impressions from the mouth of the patient and generates a cast using the impression. A digitization step S110 is then executed for providing scanned data. If casts or impressions have been obtained, they are scanned and digitized in digitization step S110. Alternately, the patient's mouth can be scanned directly, including teeth and gums, using conventional intra-oral image scanning methods, such as using an intra-oral laser scanner. Scanning and image reconstruction techniques are well known in the 3-dimensional (3-D) imaging arts. Reconstruction can use data from a scan, such as from an x-ray scan, an optical scanner, or some other imaging apparatus, such as an intraoral imaging camera, for example.

Figure 2:
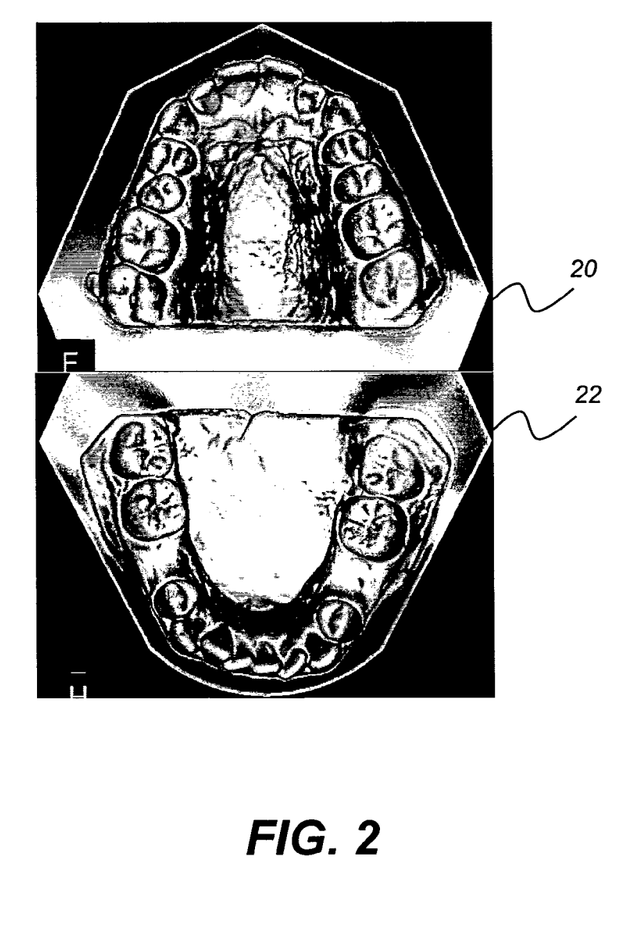
FIG. 2 shows representative dental arches obtained from a 3-D reconstruction.

By way of example, FIG. 2 shows representative virtual dental arches 20 and 22 formed and used as part of this process, using and processing impressions that were generated from a patient.

The next step in the FIG. 1 sequence is generation and display of a virtual model or data model in a model generation step S120. The reconstruction of a 3-D virtual model from acquired imaging data is well known in the dental imaging arts. The virtual or data model displays as a 3-D image. For example, U.S. Pat. No. 6,334,853 entitled "Method for obtaining a dental occlusion map" to Kopelman et al. discloses how to obtain virtual 3-D data models of a patient's teeth from a plaster model that was formed by casting a negative alginate impression. The virtual or data model can alternately be obtained from a direct scan of the patient's mouth using an intraoral camera. There are a number of commercially available intraoral cameras, including scanning intraoral cameras that utilize laser illumination. An occlusion map can then be generated from the virtual data model using the described technique. As another example, U.S. Pat. No. 7,140,877, entitled "System and method for positioning teeth" to Kaza discloses how to obtain a positive digital dental model directly from a negative deformable alginate impression by x-ray scanning of the impression.

With the virtual data model in an occlusal arrangement, maxillary and mandibular arches are in opposition in the generated data model. A generate occlusion mapping step S130 is executed, using a distribution modeling method and an optional meal data model, as described subsequently. At the completion of the mapping step S130, a display step S140 then displays the generated occlusion mapping data. As shown by dashed lines, steps S120, S130, and S140 can be repeated as necessary for different occlusion conditions.

Figure 3A:
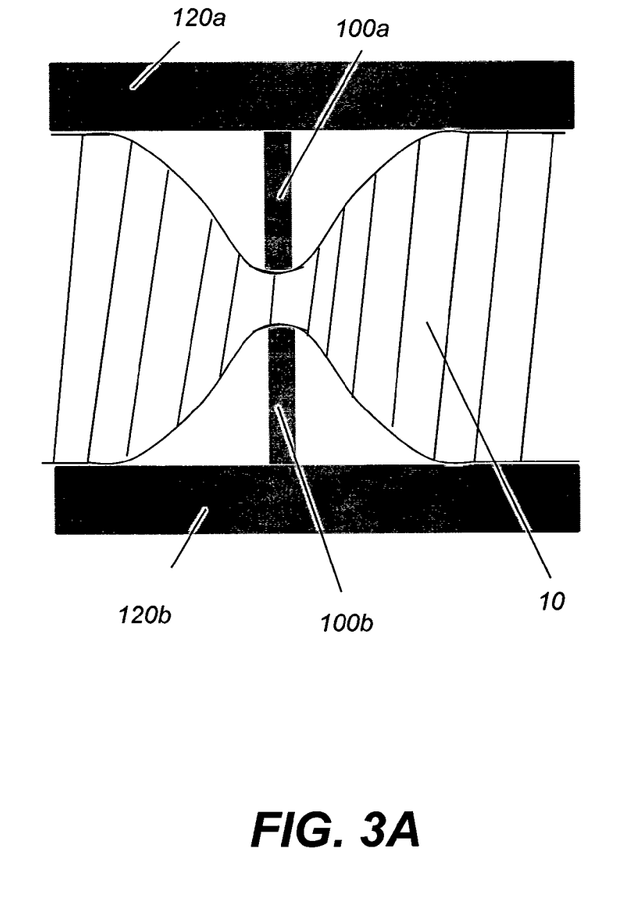
FIGS. 3A and 3B are schematic views that show tooth interaction during the chewing process.
Figure 3B:
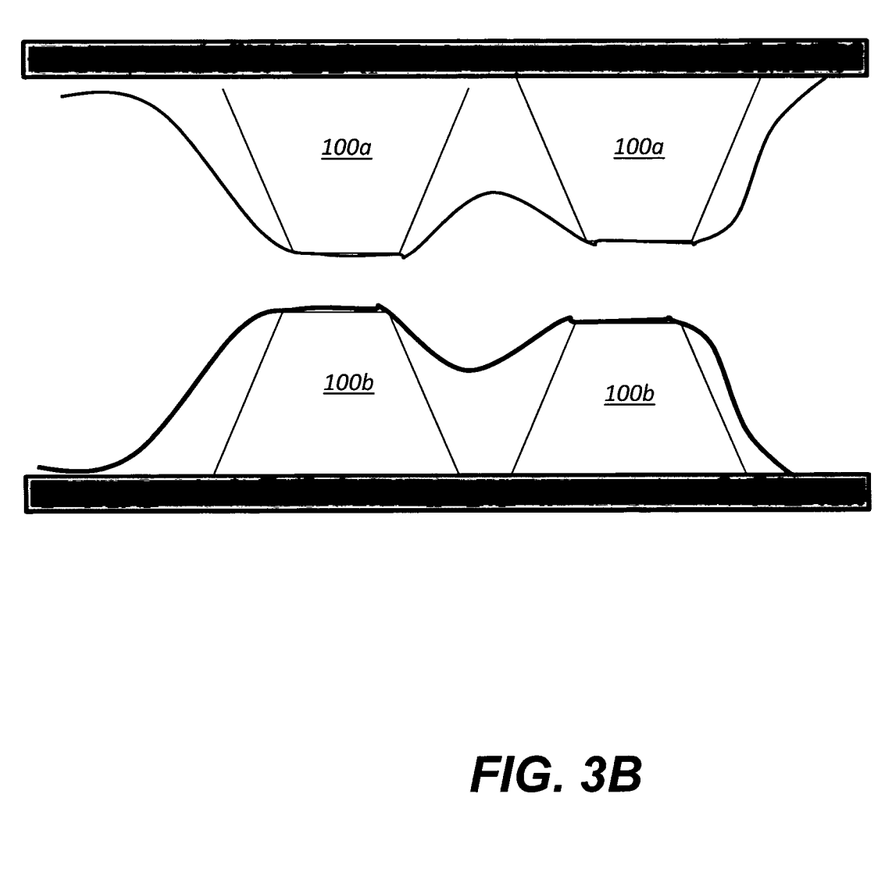
Figure 4:
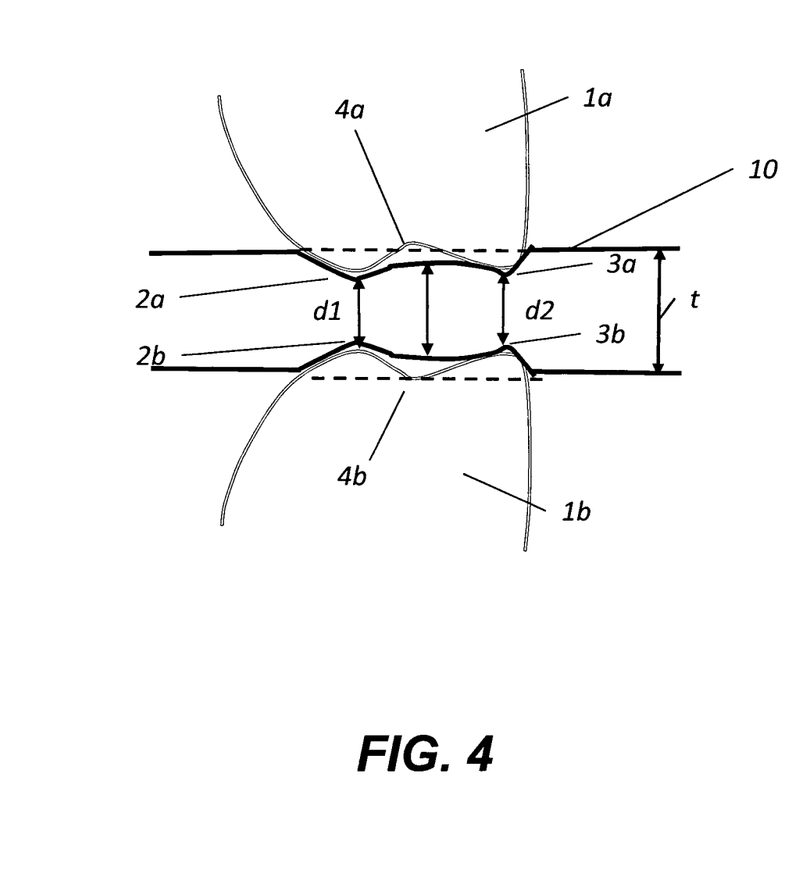
FIG. 4 is a schematic cross-sectional view for occlusal dynamics between teeth in maxillary and mandibular arches.

The schematic views of FIGS. 3A, 3B, and 4 show how the occlusion data is generated in step S130 with the maxillary and mandibular arches modeled in an occlusal relationship. A meal data model 10 or "virtual meal" is generated as a data model and used to map the pressure field distribution between opposing teeth of upper and lower jaw structures. Meal data model 10 is modeled with the parameters of an elastic, compressible foam material having predetermined elastic characteristics, density, compression characteristics, tensile strength characteristics, cell size, and the like.

According to an embodiment of the present invention, the idealized foam material used for meal data modeling has particular characteristics within the following ranges:

Density: 300-1000 $kg/m^3$;
Compression stress/strain: 0.1-3 MPa
Tensile strength: 1-100 kPa;
Cell size: 0.1-1 mm diameter In the schematic view shown in FIG. 3A, two opposite teeth 100$a$ and 100$b$ of an upper (maxillary) jaw 120$a$ and a lower (mandibular) jaw 120$b$ compress virtual foam meal data model 10. Because of the radial elastic diffusion of the pressure away from the region of minimum distance between teeth, the elastic foam does not follow the surface of teeth of the jaws. The pressure within the foam is not correlated with the distance between opposite teeth and opposite jaws. FIG. 3B presents another schematic view presenting two teeth 100$a$ and 100$b$ on each of the mandibular and maxillary arches. Elastic foam of meal data model 10 has a thickness t as shown in FIG. 4. Cusps 2$a$ and 3$a$ of a tooth 1$a$ and cusps 2$b$ and 3$b$ of a tooth 1$b$ in FIG. 4 deform foam meal data model 10, to the respective distances d1 and d2 shown. This reduces the thickness of the foam meal data model 10 from t by (t−d1) and by (t−d2) where the cusps are located.

Figure 5:
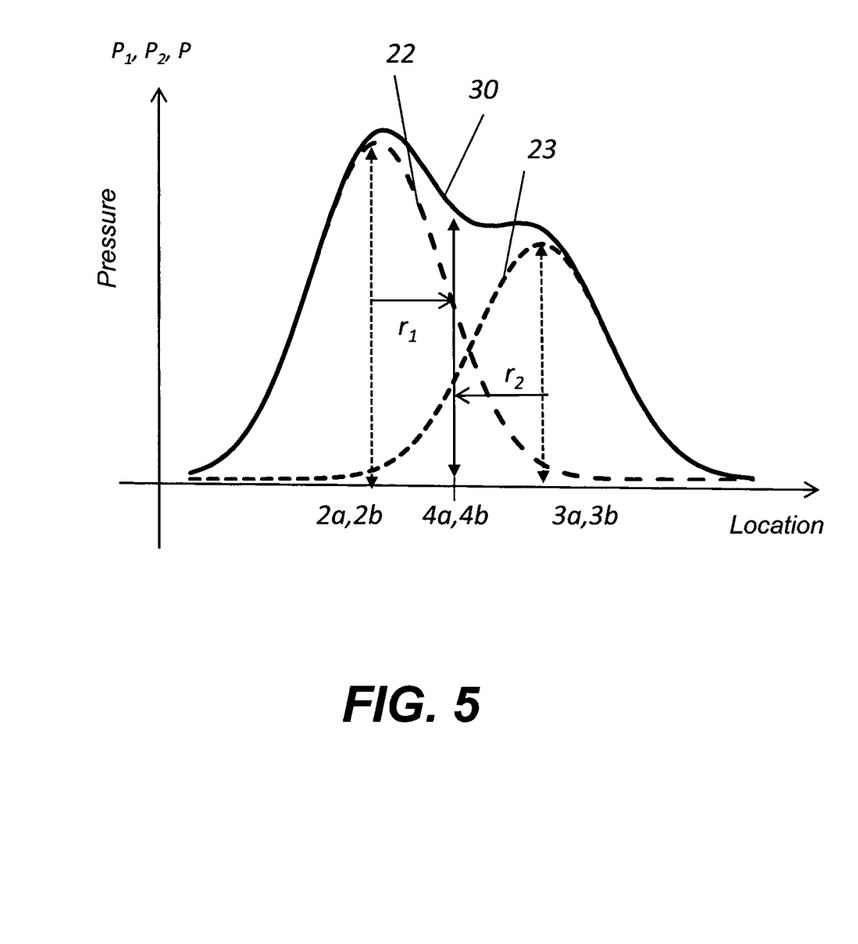
FIG. 5 is a graph showing a representative distribution for a foam meal in occlusion.

Modeling of the pressure field that is generated can be performed using any of a number of different distributions. According to an embodiment of the present invention, a Gaussian distribution is used, with an axial symmetry and with maximum intensity where the thickness of foam meal data model 10 is at a minimum. With respect to the cross-sectional view of FIG. 4, for example, maximum intensity of the pressure field distribution is in the region that is between cusps 2$a$ and 2$b$. The relative width of the Gaussian distribution is considered to be proportional to characteristics of foam meal data model 10. The graph of FIG. 5 shows a representative Gaussian distribution of pressure to spatial coordinates along a direction for foam meal data model 10 in the occlusion relationship shown in FIG. 4. Pressure fields 22 and 23 relate to pressure generated from paired cusps at 2$a$/2$b$ and 3$a$/3$b$, respectively. Pressure field 30 represents the sum of individual pressure fields: field 22 plus field 23.

It should be noted that the graph of FIG. 5 relates to a small area, representative of a single pair of opposed teeth and considered in isolation from nearby pressure fields. It can be appreciated that there are multiple surfaces that interact during occlusion and that each generated pressure field influences nearby areas as well. For any region between the teeth, the actual pressure field within that region must take into account the pressure fields generated by all of the teeth in the mouth. In addition, the actual pressure distribution also relates to the distance from each pressure field.

For the example shown in FIG. 4, the unitary pressure fields P1 and P2 created by the deformation at d1 and d2 as a function of the distance r1 and r2 from the location of maximum deformation can be expressed as:

$$P_1(r_1) = k_{meal}(t - d_1)e^{-\frac{1}{2}\left(\frac{r_1}{\sigma_{meal}}\right)^2}$$

$$P_2(r_2) = k_{meal}(t - d_2)e^{-\frac{1}{2}\left(\frac{r_2}{\sigma_{meal}}\right)^2}$$

wherein $k_{meal}$ and $\sigma_{meal}$ are constants that depend on characteristic parameters of the virtual meal model; r1 and r2 are distances from the maxima of the pressure intensity.

By varying both constants depending on the kind of meal model 10 that is used in the mouth of the patient, the dentist can assess efficiency when chewing various kinds of meal under given conditions. According to an alternate embodiment of the present invention, the constants $k_{meal}$ and $\sigma_{meal}$ are fixed in the software and the practitioner cannot change their value.

Alternate functions can be used for modeling the pressure field distribution. According to an alternate embodiment of the present invention, for example, a Lorentzian function is used:

$$P_1(r_1) = \frac{k_{meal}(t - d_1)}{1 + \left(\frac{r_1}{\Gamma_{meal}}\right)^2}$$

$$P_2(r_2) = \frac{k_{meal}(t - d_2)}{1 + \left(\frac{r_2}{\Gamma_{meal}}\right)^2}$$

wherein $k_{meal}$ is constant depending on the meal type and represents the width of the pressure field distribution. $\Gamma_{meal}$ is a constant, depending on the meal type and represents the width of the pressure field distribution.

A pressure field distribution can also be calculated using more complete mechanical equations. In particular, the pressure field distribution can be expressed as a function of the elastic Young modulus and the Poisson coefficient. Other bell-shaped functions, including axially symmetric functions, can also be contemplated for providing a model of the pressure field distribution.

In the examples above, the maximum of the field is proportional to the maximum of the deformation of the virtual foam meal model 10, expressed as $(t-d_1)$ and $(t-d_2)$, respectively, corresponding to an elastic deformation. A non-linear relationship between the maximum of the pressure field distribution and the maximum of the local deformation can also be contemplated.

According to an embodiment of the invention, the total pressure field created by the deformation to d1 and d2 is the sum pressure field 30 of individual unitary pressure fields 22, 23. That is, $$P(r1,r2) = P1(r1) + P2(r2).$$

This calculation can be extended for all pressure fields in the mouth. The pressure field calculation depends, in part, on the thickness and other features of the foam data model.

In the example of FIGS. 4 and 5, the distance between opposite teeth surface is high at the location 4a, 4b that corresponds to the groove of the teeth. Nevertheless, as the graph of FIG. 5 shows, the pressure is non-zero in this region of the foam model. Both nearby pressure fields P1 and P2 influence the pressure between locations 4a and 4b and their combined effect can be sensed at this point. This demonstrates that merely determining distances between the occlusal surfaces of opposite teeth fails to provide all the relevant information for assessing the efficiency of chewing in given occlusal conditions. This is especially the case for meals for which the width of the unitary pressure fields ($\sigma_{meal}$ and $\Gamma_{meal}$ for the Gaussian and Lorentzian distribution respectively) is higher than the average distance between cusps and ridges.

Figure 6:
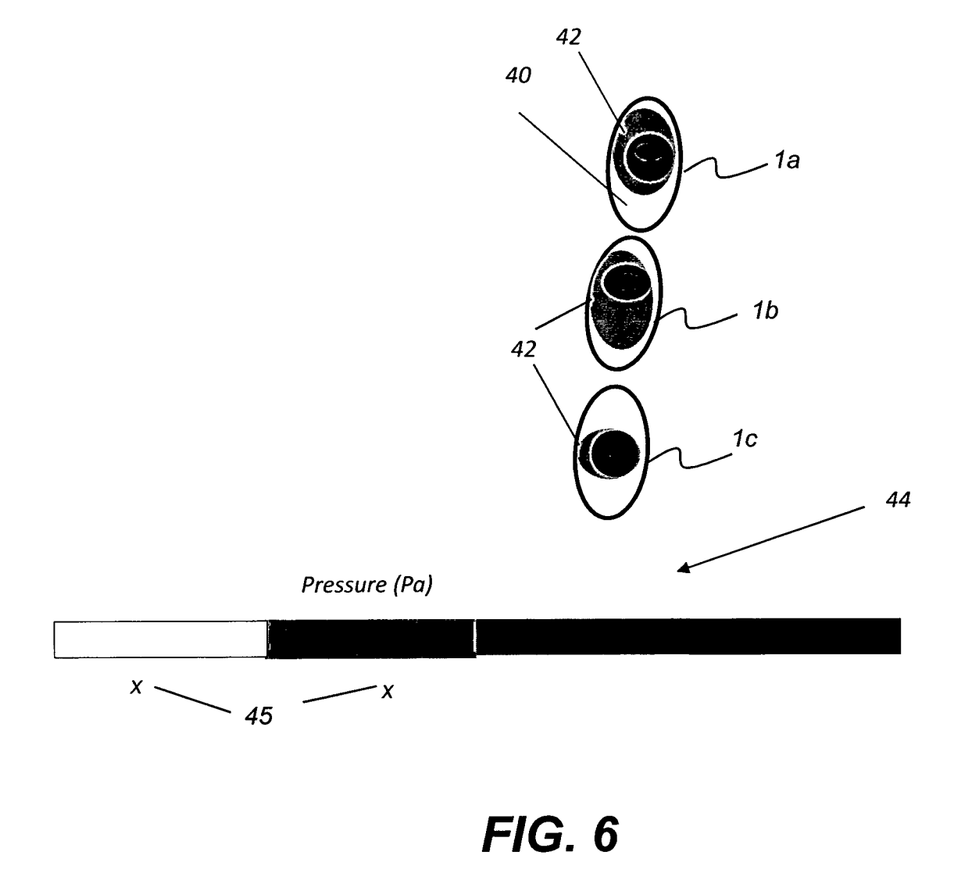
FIG. 6 is a representative mapping for a pressure field distribution in an occlusion relationship.

After obtaining pressure field data modeled from opposing teeth, the complete pressure field distribution for the specific occlusal relationship can be mapped, as shown in FIG. 6. The map is projected on the occlusal surface 40 of the teeth of at least one virtual arch, with teeth 1a, 1b, and 1c shown in FIG. 6. The map is composed of color-coded or grayscale-coded surfaces 42. Different value ranges for the pressure field distribution display in different colors according to an embodiment of the present invention; alternately, different gray scales are used for distinguishing pressure levels. A legend 44 below this field mapping example is labeled with values 45 to provide the user with the correspondence between the color or grey level of this mapping and the pressure in the foam at the vertical location of the point of the occlusal surface where the map is projected.

Techniques for 3-D computer modeling of a compressible foam material to map one or more radial pressure fields from points of compression are familiar to those skilled in the material modeling arts. Software tools for this type of analysis include finite element analysis software, such as Abaqus FEA, a product of Dassault Systemes, Vélizy-Villacoublay, FR. Dedicated software of this type can be applied to a virtual model of upper or lower dental arches to calculate the pressure in each point of a material compressed between both arches.

Figure 7:
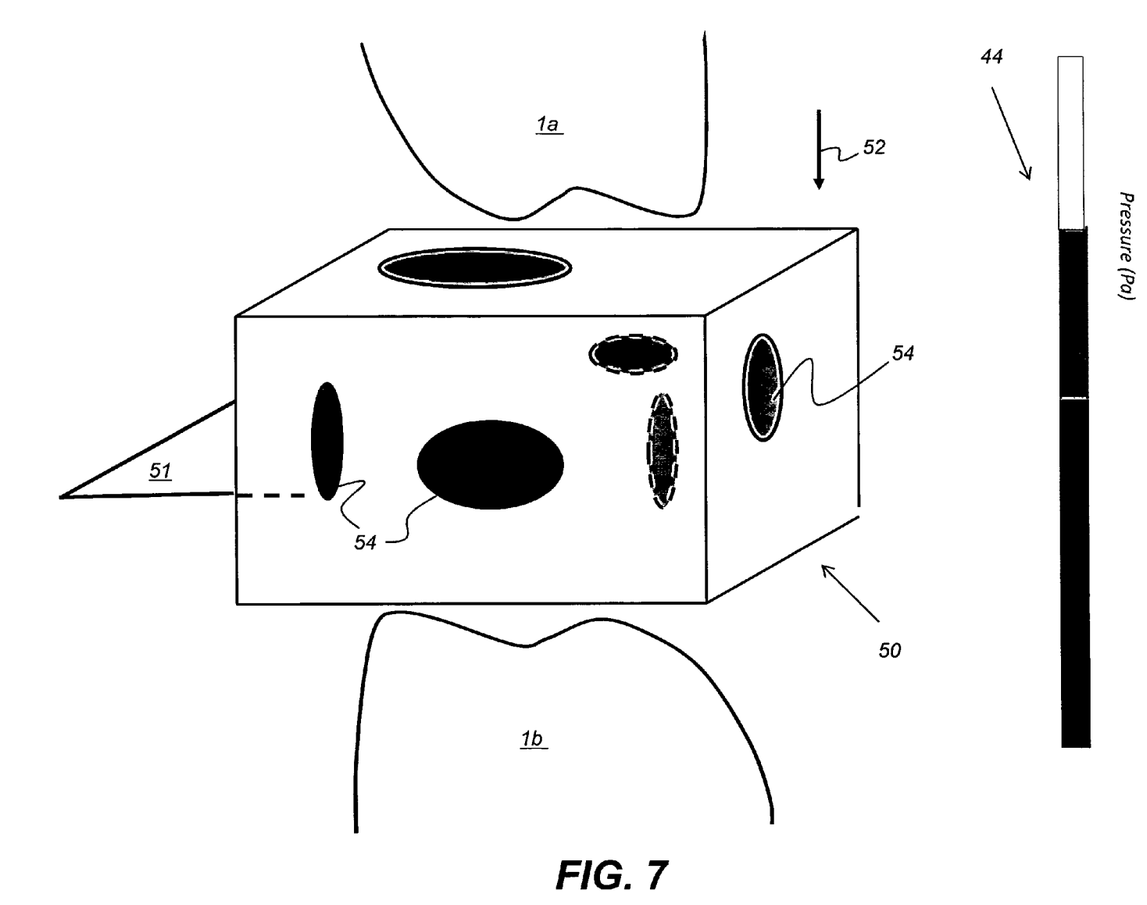
FIG. 7 is a schematic representation of three-dimensional (3-D) occlusion dynamics.

Referring to the schematic representation of a block of material 50 in FIG. 7, a 3-D (3-dimensional) pressure field is represented. The pressure field calculated at a given horizontal position (horizontal plane 51 in FIG. 7) can be projected on the occlusal surface of teeth 1a, 1b. The pressure inside the material can be averaged along a direction 52 that may or may not be perpendicular to the occlusal surface of teeth 1a and 1b, and then projected on the occlusal surface of the teeth of either the upper or lower dental arch. Pressure fields 54 can be identified and characterized at different locations relative to block of material 50. For projection onto the tooth surface, the processing logic either determines the pressure value relative to a cross section along horizontal plane 51 or averages the value of a 3-D matrix of pressure values along a direction 52. Where the pressure value relative to plane 51 is generated, pressure field values along the plane can be identified and mapped onto the display of occlusal surfaces of the teeth. The display can show calculated pressure values using color or grayscale levels from legend 44 as shown and described with reference to FIG. 6. Similarly, where the pressure value relative to direction 52 is computed, the average pressure value can be displayed at one or more appropriate locations on the tooth surface, relative to the direction vector. Block of material 50 used for this modeling has predetermined characteristics for response to occlusion pressure. According to an alternate embodiment of the present invention, the operator can adjust the characteristics of the block of material 50.

Consistent with an embodiment of the present invention, a computer executes a program with stored instructions that perform on image data accessed from an electronic memory to generate the various data models and calculate corresponding pressure field distributions as previously described. As can be appreciated by those skilled in the image processing arts, a computer program of an embodiment of the present invention can be utilized by a suitable, general-purpose computer system, such as a personal computer or workstation, as well as by a microprocessor or other dedicated processor or programmable logic device. However, many other types of computer systems can be used to execute the computer program of the present invention, including networked processors. The computer program for performing the method of the present invention may be stored in a computer readable storage medium. This medium may comprise, for example; magnetic storage media such as a magnetic disk (such as a hard drive) or magnetic tape or other portable type of magnetic disk; optical storage media such as an optical disc, optical tape, or machine readable bar code; solid state electronic storage devices such as random access memory (RAM), or read only memory (ROM); or any other physical device or medium employed to store a computer program. The computer program for performing the method of the present invention may also be stored on computer readable storage medium that is connected to the image processor by way of the internet or other communication medium. Those skilled in the art will readily recognize that the equivalent of such a computer program product may also be constructed in hardware.

It will be understood that the computer program product of the present invention may make use of various image manipulation algorithms and processes that are well known. It will be further understood that the computer program product embodiment of the present invention may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with the computer program product of the present invention, are not specifically shown or described herein and may be selected from such algorithms, systems, hardware, components and elements known in the art.

It should be noted that the term "memory", equivalent to "computer-accessible memory" in the context of the present disclosure, can refer to any type of temporary or more enduring data storage workspace used for storing and operating upon image data and accessible to a computer system. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Display data, for example, is typically stored in a temporary storage buffer that is directly associated with a display device and is periodically refreshed as needed in order to provide displayed data. This temporary storage buffer can also be considered to be a memory, as the term is used in the present disclosure. Memory is also used as the data workspace for executing processes and for recording entered values, such as seed points, or storing intermediate and final results of calculations and other processing. Computer-accessible memory can be volatile, non-volatile, or a hybrid combination of volatile and non-volatile types. Computer-accessible memory of various types is provided on different components throughout the system for storing or recording, processing, transferring, and displaying data, and for other functions.

The invention has been described in detail with particular reference to a presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

The invention claimed is:

1. A method for generating a mapping of dental occlusion, the method comprising:
   generating a three-dimensional data model of the patient's teeth according to acquired image data;
   positioning maxillary and mandibular arches in opposition in the generated data model of the patient's teeth;
   generating a meal data model having characteristics of a foam material;
   calculating a pressure field distribution for the generated meal data model for one or more pairs of opposed teeth from the generated three-dimensional data model of the patient's teeth; and
   displaying at least a portion of the calculated pressure field distribution.

2. The method of claim 1 wherein calculating the pressure field distribution comprises combining modeled information from occlusion at multiple surfaces.

3. The method of claim 1 wherein the pressure field distribution is a Gaussian or a Lorentzian distribution.

4. The method of claim 1 wherein the meal data model comprises values for one or more of density, compression, tensile strength, and cell size.

5. The method of claim 1 wherein the pressure field distribution is calculated as a function of the elastic Young modulus and the Poisson coefficient.

6. The method of claim 1 wherein displaying the calculated pressure field distribution comprises displaying different value ranges in different colors.

7. The method of claim 1 wherein displaying the calculated pressure field distribution comprises displaying the distribution overlaid on an image of the maxillary or mandibular arch.

8. The method of claim 1 further comprising repositioning the maxillary and mandibular arches in opposition in the data model of the patient's teeth and repeating steps of generating the meal data model, calculating the pressure field distribution, and displaying the calculated distribution.

9. The method of claim 1 wherein obtaining digital image data further comprises forming one or more casts or impressions from the mouth of the patient and scanning the one or more casts or impressions using x-rays.

10. The method of claim 1 wherein obtaining digital image data further comprises scanning the mouth of the patient using an intra-oral scanner.

11. The method of claim 1 wherein displaying at least the calculated pressure field distribution comprises displaying a grayscale image.

12. The method of claim 1 wherein calculating the pressure field distribution comprises generating a three-dimensional pressure field relative to a block of material.

13. The method of claim 12 wherein generating the three-dimensional pressure field further comprises averaging the pressure along a predetermined direction.

14. The method of claim 12 wherein generating the three-dimensional pressure field further comprises identifying the pressure along a plane relative to the tooth surface.

15. A method for generating a mapping of dental occlusion of a patient's teeth, the method comprising:
   generating a three-dimensional data model of the patient's teeth;
   positioning maxillary and mandibular arches in opposition in the generated data model of the patient's teeth;
   calculating one or more distances between occlusal surfaces of opposed teeth according to the maxillary and mandibular arch positioning;
   generating a meal data model having characteristics of a foam material;
   calculating a pressure field distribution for the generated meal data model for one or more pairs of opposed teeth according to the generated data model of the patient's teeth and according to the one or more calculated distances between occlusal surfaces; and
   displaying at least the calculated pressure field distribution for one or more of the teeth.

16. The method of claim 15 wherein the calculated pressure field is calculated using one or more axially symmetric functions.

17. The method of claim 15 wherein generating a three-dimensional model of the patient's teeth further comprises obtaining one or more casts or impressions of the patient's maxillary and mandibular arches and scanning the one or more casts or impressions using x-rays.

18. A method for generating a mapping of dental occlusion, the method comprising:
   generating a three-dimensional data model of the patient's teeth using one or more casts or impressions of the patient's maxillary and mandibular arches and using digital image data from the one or more casts or impressions;
   positioning the maxillary and mandibular arches in opposition in the generated data model of the patient's teeth;
   calculating one or more distances between occlusal surfaces of opposed teeth according to the maxillary and mandibular arch positioning;
   generating a meal data model having characteristics of a foam material;
   calculating a pressure field distribution for the generated meal data model for one or more pairs of opposed teeth according to the generated data model of the patient's teeth and according to the one or more calculated distances between occlusal surfaces; and
   displaying at least a portion of the calculated pressure field distribution.

* * * * *